US00PP09045P

United States Patent [19]

Kent

[11] Patent Number: Plant 9,045

[45] Date of Patent: Jan. 17, 1995

[54] BROMELIAD PLANT 'GUZ 209'

[75] Inventor: Jeffrey C. Kent, Vista, Calif.

[73] Assignee: Kent's Bromeliad Nursery, Inc., Vista, Calif.

[21] Appl. No.: 152,030

[22] Filed: Nov. 15, 1993

[51] Int. Cl.[6] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Frank B. Robb

[57] ABSTRACT

A Bromeliad plant of the Guzmania type which is distinctive because of the pink blush of the floral bracts which are long lasting. This pink blush is not found in other plants of this type.

1 Drawing Sheet

This invention relates to Bromeliads, a colorful indoor plant.

The development of new varieties with improved characteristics has been an ongoing object of an extensive program to provide new plants of all of the types known as Aechmea, Guzmania, Vriesea, and Neoregelia, the present plant being of the Guzmania type having several outstanding characteristics.

In the program of development with which I have been associated, we have caused extensive breeding and cross breeding to take place and in the plant which will be described in detail hereinafter, several of the most prominent characteristics have been embodied, the new plant being identified as Guz 209 for the basic reason that it is in fact a Guzmania, which was produced from the seed parent Guzmania Minor, Equador, and the pollen parent Guzmania Squarrosa, Pink, neither of which is patented.

The parents in this plant were grown by seed, field collected in Ecuador, and were selected from a number of seedlings. It is highly unlikely that these specific parents are available to other hybridizers since the parent plants have not been released nor is it my practice to give such release. Cleistogamy has not been observed in any of the seedlings produced by the union of these two selected parents, nor does the stamen produce viable pollen.

Guzmania minor is a highly variable species as to size of plant and color and proportional shape of the inflorescence. The inflorescence is an umbel, and the white cylindrical corollas are subtended by red to orange bracts. The leaves are medium green lanceolate, and form a basal rosette that is narrowly upright in profile. The seed parent clone selected for this cross is quite small compared to others of this species. The largest leaf, at anthesis, is 6"×7/16". The largest floral bract is $1\frac{1}{2}$×7/16" diminishing in size to the apex of the inflorescence which is 7". The bracts are mandarin red #24 in color (Maerz and Paul "Dictionary of Color") at anthesis.

The pollen parent clone is of a highly variable species, particularly in the color of the floral bracts. These may be yellow, red, magenta, purple or bicolored in shades of red and yellow. The pollen parent clone of this cross is medium sized for the species. The leaves and lanceolate form a basal rosette, somewhat spreading. The color of the largest leaf at anthesis is medium green. The inflorescence is a branched raceme, pyramidal in shape. Each branch bears a glomerule of cylindrical yellow corollas. The height of the plant including the inflorescence is 16" at anthesis.

Generally plants of the Bromeliad family are notable for the color, shape, and size of their floral bracts, and not particularly for the form of the plant, color and size of flowers.

However, the floral bracts on this new plants and described in detail, are a shade of pink not found in Bromeliads which are solid as house plants, in my experience. Usually other plants of this type are more purple/pink.

The color in the bracts of this new plant lasts for three months with very little if any diminution.

I have caused this new plant to be reproduced by tissue culture in the vicinity of Rancho Santa Fe, Calif., and found the same to come true in successive generations. I therefore conclude that it is a desirable plant as an indoor flowering plant for decorative purposes as well as for other reasons for which such plants may be used.

As is shown in the accompanying drawing, a typical plant of my new variety is represented photographically and as such is as nearly like the plant can be illustrated by such process and is recognizably reasonably accurate to show the pink color which was sought to be reproduced.

The drawing depicts the size of the bracts in comparison to the size of the leaves, and the character of both plant and inflorescence and shows the position and the essentially hidden aspect of the flower parts which are inserted between the basal portion of the bract and the stem of the scape. The color fidelity of the drawing is as accurate as can be produced with color reproductions of this type.

In addition, certain details of the plant are set forth in the following descriptive notations which have been established as typical and support the reference to the plant as outstanding therefore.

Reference to color where appropriate is made by comparison to the Nickerson Color Fan published by Munsell Color Co., Inc.

Classification:

*Name under which it will be known in commerce.*—Guz 209. Monocot, perennial. Medium, small, vigorous, upright, spreading, dense, vase formed, and tender. The plant is sterile.

*Overall height.*—13 to 15 inches, including inflorescence.

*Overall width.*—14 to 16 inches. The plant described is upright to somewhat spreading in conformation.

Leaves:

*Length.*—10 to 13 inches.

*Width.*—$\frac{7}{8}$ inches. Linear, acuminate, abruptly pointed, acutely pointed, medium, and smooth.

*Margin.*—Smooth.

Flower buds: Tender, small, medium, obtuse, and appressed.

Floral bracts: Linear acute $3\frac{1}{2}'' \times 1''$ at base of inflorescence, decreasing in size to $1\frac{1}{2}'' \times \frac{3}{4}''$ at apex. The lower bracts, those that surround the stem below those that actually subtend the flowers, are dark red 2.5R 3/7 at the base. The rest of these bracts as well as those up the peduncle to its apex are deep pink 2.5 6/11.

*Color.*—Deep pink 2.5R 6/11 grading to dark red 2.5R 3/7 at base of upper bracts. The bract color begins as a pale wash of light pink, deepening towards anthesis to a solid pink. After anthesis is virtually a reversal to a pale wash of light pink.

Flowers: Cylindrical corolla, brilliant yellow 5y9/9 at anthesis. The length of time from deflasking the plantlets to flowering, is approximately sixteen months. Ethylene gas is used to initiate flowering and takes approximately twenty weeks to flowering. No work has been done, or observations made to note variations in flowering due to environmental conditions.

Plants of the Bromeliad family are most often selected for the color, shape, and size of their floral bracts rather than for the conformation of the plant, leaves, or the color shade and size of the flowers. The floral bracts on Guz 209 are of a shade of pink not often found in Bromeliads sold as house plants, the others are more of a purple/pink. The color in the bracts lasts three months.

I claim:

1. A new and distinct variety of Bromeliad plant as shown and described, characterized particularly as to novelty by the pink blush of the floral bracts, its value as a house plant distinct from other Bromeliads, and the long lastingness of the color in said bracts.

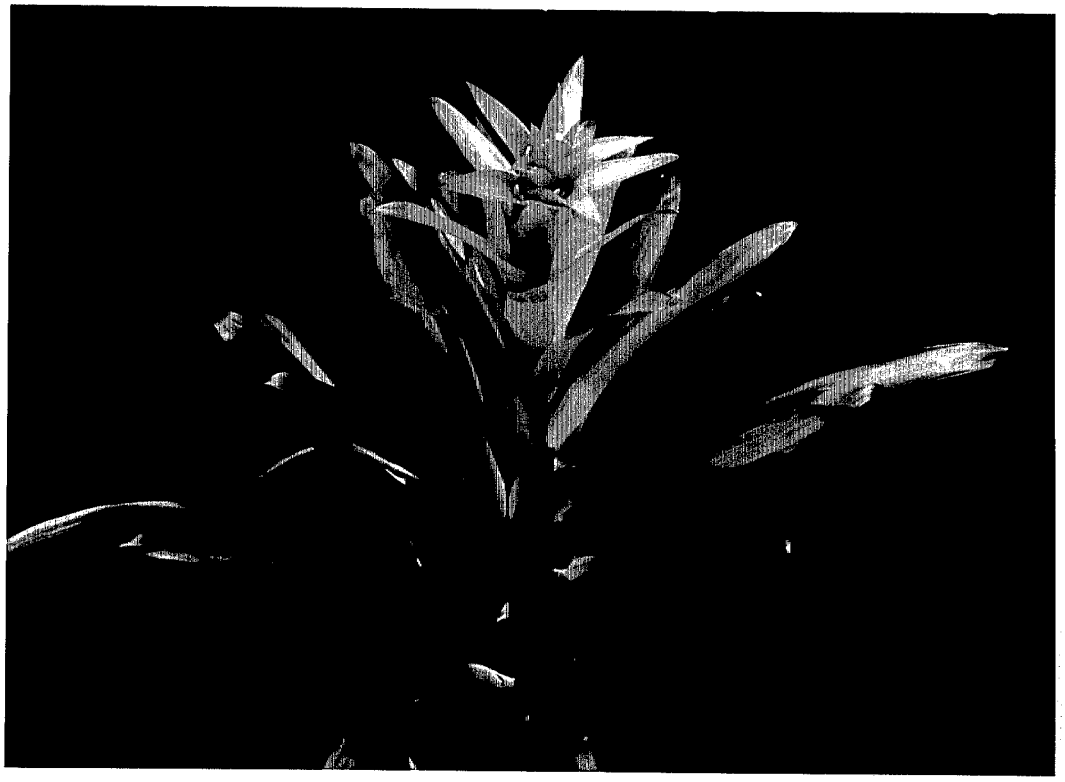

* * * * *